United States Patent
Steinbach et al.

[11] Patent Number: 5,814,019
[45] Date of Patent: Sep. 29, 1998

[54] IMPLANTABLE INFUSION PUMP

[75] Inventors: Bernd Steinbach; Claus Walter, both of Bad Homburg, Germany

[73] Assignee: Fresenius AG, Germany

[21] Appl. No.: 618,431

[22] Filed: Mar. 15, 1996

[30] Foreign Application Priority Data

Mar. 17, 1995 [DE] Germany ............... 195 09 634.7

[51] Int. Cl.⁶ ...................................... A61N 31/00
[52] U.S. Cl. ............................... 604/131; 604/141
[58] Field of Search ........................... 604/131, 132, 604/140, 141, 143, 145

[56] References Cited

U.S. PATENT DOCUMENTS

| | | | |
|---|---|---|---|
| 4,969,873 | 11/1990 | Steinbach et al. | 604/145 |
| 5,167,633 | 12/1992 | Mann et al. | 604/141 |
| 5,306,257 | 4/1994 | Zdeb | 604/131 |
| 5,336,194 | 8/1994 | Polaschegg et al. | 604/132 |
| 5,514,103 | 5/1996 | Srisathapat et al. | 604/141 |
| 5,578,005 | 11/1996 | Sancoff et al. | 604/132 |

*Primary Examiner*—Michael A. Brown

[57] ABSTRACT

The invention refers to an implantable infusion pump for the dosed administration of medication into the human body comprising a pump chamber which is formed by a lower chamber part and an upper chamber part connected thereto, whereby the pumping chamber is divided into two subchambers by a gas impermeable flexible partition and provided as a reservoir for medicinal solutions, the upper chamber part has a refilling opening which is sealed by at least a pierceable septum and the reservoir for medicinal solutions is connected to an outlet catheter via an outlet opening and possibly an outlet reduction arrangement, and the second subchamber is delimited by the lower chamber part and the flexible partition to serve as a pressure chamber to accommodate a propellant, whereby the gas impermeable partition is a convex metal foil following the contour of the inner form of the upper part of the chamber. This metal foil may be covered on one or both sides with a polymer support film.

16 Claims, 3 Drawing Sheets

IMPLANTABLE INFUSION PUMP

BACKGROUND OF THE INVENTION

Field of the Invention

The present invention concerns an implantable infusion pump for the dosed dispensing of medication into the human body.

Implantable infusion pumps are already known. The implantable infusion pump known from DE 39 15 251 A1 has a pumping chamber which is formed by a shell-shaped lower part of the chamber and an upper part of the chamber connected thereto. The pumping chamber is divided into two subchambers by means of a flexible membrane. The first subchamber is delimited by the upper chamber part and the membrane and designed as a reservoir for the medication. The upper part of the chamber includes a refilling opening which is sealed with a pierceable septum. The septum is jammed between a septum holder connected to the upper part of the chamber and the upper part of the chamber. The medication reservoir is connected by an outlet catheter via an outlet opening and possibly an outlet reduction arrangement. The second subchamber is delimited by the lower part of the chamber and the membrane and designed as a pressure chamber to accommodate a propellant that expands at body temperature.

Infusion pumps with a similar structure are further known from DE 26 04 113 A1 and DE 21 24 062 B2 as well as from DE 4038 049 A1. An additional infusion pump is described in DE 44 32 991 A1 which is hereby expressively referred to for the purpose of disclosure.

The pump components in these infusion pumps are made of biocompatible metal alloys or plastics material and they are connected to each other by means of welding joints or snap-in joints.

Implantable infusion pumps are disposed in a subcutaneous pocket in the area of the abdomen of the patient whereby the refill opening sealed by the septum is palpable under the skin of the patient. The medication reservoir is filled by piercing the skin of the patient and the septum with an appropriate needle of a syringe. Due to the pressure in the syringe, the medication or the medicinal solution flows into the medication reservoir through the needle.

Implantable infusion pumps are used for the continuous medication (constant dosage) for relatively long periods of time in patients who otherwise could be treated by injection of the medications only, such as morphines, heparines and the like, several times daily. These pumps are advantageous in comparison with injections in that the dose administered no longer has to be overdosed to the extent that it does not fall below a certain minimal dosage by the next administration time despite the decomposition of the medication, but that a uniform flow and a significantly lower total supply of the drug can be realized. Such infusion pumps, in particular in the case of the administration of pain relievers, are subject to strict safety requirements. Possible over or under dose must be avoided. Depending on the drug administered, an overdose, may result in a high health risk, or have a lethal effect, in particular with pain relievers.

The mode of action in an implantable infusion pump is essentially that the propellant contained in the pump, having a boiling point below body temperature, partially evaporates subsequent to the implantation of the pump into the body of the patient, exerting pressure on the drug in the medication reservoir via the separating partition, or, for example, a flexible membrane or a bellows, whereupon the medication or the medicinal solution flows to the target organ via a reduction system and a catheter. Hereby the volume of the medication compartment diminishes while the propellant compartment increases. The volume increase of the propellant compartment is equalized by the further evaporation of the propellant and takes place at a constant temperature isobar, as long as the propellant provided is a two phase system and no foreign gases exist in the propellant compartment. The isobaric pressure development is necessary for the systems in order to maintain a constant output rate.

Bellows made of non-rusting metal, such as titanium, used as a partition in prior art implantable infusion pumps are very expensive. On the other hand, partitions made of plastic composite films which are substantially more cost effective are, as investigations showed, unable to prevent a diffusion of the propellant from the propellant chamber into the medication chamber and a diffusion of gases and vapor from the medication chamber into the propellant chamber. Furthermore, chloridated fluorohydrocabons which usually are used as propellant are extremely aggressive with regard to plastic materials and thus diminish their stability.

SUMMARY OF THE INVENTION

The preceding and other shortcomings of prior art methods and systems are overcome by the present invention which provides an implantable infusion pump for the dosed administration of medications into the human body, with a pumping chamber, which is formed by an lower chamber part and an upper chamber part connected thereto, whereby the pumping chamber is divided by a gas impermeable flexible partition into two subchambers, the first subchamber is delimited by the upper chamber part and the flexible partition and is designed as a reservoir for medicinal solutions, the upper part of the chamber has with a refill opening which is sealed by at least one pierceable septum, and the reservoir for medicinal solutions is connected to an outlet catheter via an outlet opening and possibly an outlet reduction arrangement, and the second subchamber is delimited by the lower chamber part and the flexible partition and is designed as a pressure chamber to accommodate a propellant, characterized, in that the gas impermeable flexible divider is a convex metal foil following the contour of the inner form of the upper part of the chamber.

The foregoing and additional features and advantages of this invention will become apparent from the detailed description and accompanying drawing figures that follow. In the figures and written description, numerals indicate the various features of the invention, like numerals referring to like features throughout for both the drawing figures and the written description.

DETAILED DESCRIPTION OF THE PREFERRED EMBODIMENTS

Figure 1:
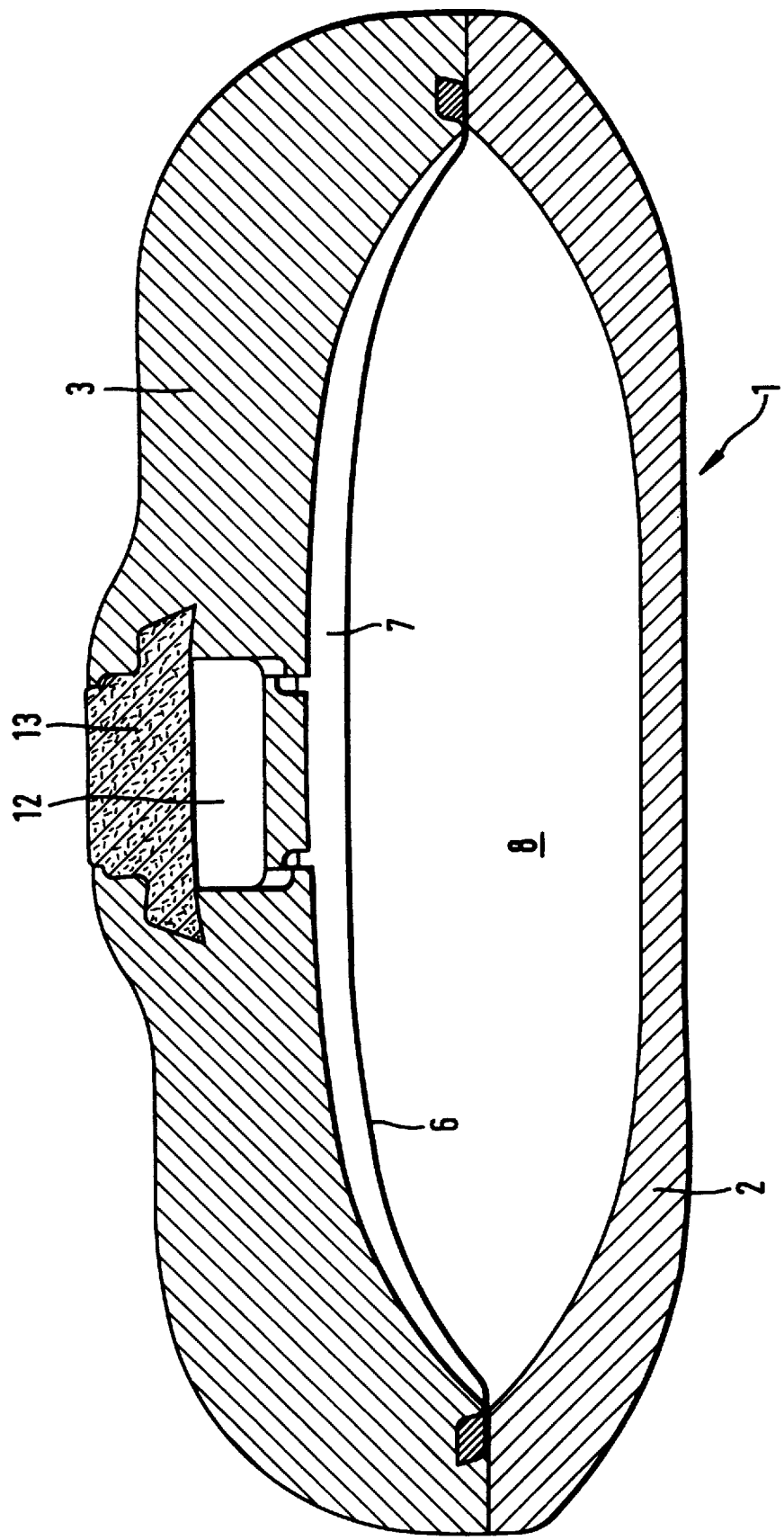
FIG. 1 represents a vertical section through a schematically depicted implantable infusion pump according to the invention.

The object of this invention to provide an implantable infusion pump with which gas diffusion (propellant on the one hand and gases and water vapor on the other) through the partition between the medication reservoir and the pressure chamber containing the propellant is essentially eliminated and a constant pumping rate of the medication is guaranteed for the entire operating time, which is compatible with medications, easily filled with medications, simple and safe to handle, made of biocompatible materials and of mutually compatible materials and which can be produced simply and cost effectively.

According to the invention this object is accomplished in an infusion pump of the type mentioned in the introduction in that the gas impermeable flexible partition is a convex metal foil following the contour of the inner form of the upper chamber part.

According to the invention the metal foil used as a partition is convex in accordance with its following of the contour of the inner form of the upper chamber part (and correspondingly of the lower chamber part) and flexible and free of stress. This convex, or dome-shaped, design of the foil, may be achieved in any suitable manner, for instance, in a deep drawing process where the foil is adapted to the inner shape of the upper chamber part (and correspondingly of the lower chamber part) of the housing of the infusion pump.

The metal foil may be made of any metal suitable for this purpose, whereby foils of aluminum, gold, silver, titanium or platinum are preferred. In particular, an aluminum foil is preferred. The thickness of the foil must be such that the blocking effect is guaranteed and also that the foil will not buckle. The suitable thickness of the metal foil is in the range of 1–100 $\mu$m, preferably in the range of 3–40 $\mu$m and in particular in the range of 5–20 $\mu$m.

According to an additional embodiment the metal foil can be provided with a coating of a polymer support film on the side facing the medication or the medicinal solution. Suitably a polyurethane may be used as an adhesive. Polymer materials which possess good medication compatibility and also have good blocking characteristics against water vapor, oxygen and $CO_2$ are suitable as supports. According to the invention, films made of polyethyleneterephthalate are preferred. The thickness of these films is suitably in the range of 1–100 $\mu$m, preferably 30–40 $\mu$m and in particular 5–20 $\mu$m and may, for example, be 12 $\mu$m.

According to an additional embodiment the metal foil can be provided, according to the invention, with a coating of a support film on the side facing the propellant whereby, for example, suitably a polyurethane may be used as an adhesive. Polymer materials which are compatible with the propellant and also provide good blocking characteristics against the propellant are suitable as supports. According to the invention, films made, for example, of polyolefins or polyamides are suitable, whereby polyolefins are preferred. Among the polyolefin films, films made of polyethylene or polypropylene are preferred, whereby films made of polyethylene are preferred in particular. The thickness of these films is suitably in the range of 2–400 $\mu$m, preferably 10–100 $\mu$m and in particular 25–100 $\mu$m and may, for example, be 70 $\mu$m.

According to an additional, preferred, embodiment of the invention the metal foil can be provided with a coating of a support lamination on both sides whereby the above mentioned films are each disposed on the appropriate side. Thus the metal foil on the side facing the medicinal solution may be coated with a film of polyethyleneterephthalat and the one on the side facing the propellant with a polyolefine film, such as a polyethylene film. Such a lamination system—viewed from the medication reservoir—may preferably be structured as follows:

a) film of polyethyleneterphthalate, thickness 12 $\mu$m b) metal foil, preferably aluminum foil, thickness 12 $\mu$m c) polyethylene film, thickness 70 $\mu$m The polymer support films increase the bending radii and thus reduce the tendency to buckle.

According to an additional embodiment of the invention, the partition may be designed as a film system whereby on the side of the aforementioned metal foil or metal lamination foil facing the medicinal solution, a polymer film with good blocking characteristics against water vapor and/or a polymer film with good medication compatibility and blocking characteristics against water vapor, oxygen and $CO_2$ is additionally disposed, whereby, if the two additional films are present, the polymer film with good drug compatibility comes in contact with the medicinal solution, and the polymer film with good blocking characteristics against water vapor is disposed between the polymer film with good drug compatibility and the metal foil or metal composite film. Preferably, both additional films for the metal, or metal composite film are present.

As a film with good drug compatibility and blocking characteristics against water vapor, oxygen and $CO_2$, a polyethyleneterphthalat film is particularly suitable. The thickness of these films is suitably in the range of 2–400 $\mu$m, preferably having a thickness of 25–250 $\mu$m and in particular within the range of 40–150 $\mu$m and may, for example, be 100 $\mu$m thick. As a film with good blocking characteristics against water vapor, any polymer film which has these characteristics is suitable, whereby a polychlortrifluoroethylene film is particularly preferred. The thickness of these films is suitably in the range of 2–400 $\mu$m, preferably having a thickness of 25–250 $\mu$m and in particular within the range of 40–150 $\mu$m and may, for example, be 127 $\mu$m thick.

The two additional films may (if both are present) be connected with or glued to each other and to the metal foil or the metal composite film over the entire surface or only in the edge area, e.g., edge welded or glued, whereby the edge connection is preferred.

A particularly preferred film system—seen from the medication reservoir—is composed as follows:

a) film made of polyethyleneterphthalate, b) film made of polychlorotrifluoroethylene c) composite film made of i) polyethyleneterphthalate film ii) metal foil, preferably aluminum foil iii) polyolefin film, preferably polyethylene film whereby the films are used in the aforementioned thicknesses. This film system is also convex in accordance with its following the contour of the inner form of the upper chamber part (and correspondingly of the lower chamber part) and flexible and free of stress. This convex design of the film system is obtained in the already aforementioned manner.

The partition used is conventionally securely pressed or jammed in its edge area between the edge areas between the upper part of the chamber and the lower part of the chamber.

According to a particularly preferred embodiment, a metal foil or a lamination metal film or a metal foil system as described above may be disposed within the infusion pump in addition to the above-described gas impermeable partition made of the metal foil or lamination metal foil or the aforementioned film system between the propellant and the inner wall of the lower part of the chamber. The metal foil or the metal lamination film or the film system is convex following the contour of the inner form of the lower chamber part, whereby this convex design may be achieved in the previously described manner. This additional metal foil or the metal lamination film or the additional film system is connected with the flexible gas impermeable partition used according to the invention in the edge area along the entire circumference, for example, by means of edge welding or glueing. The resultant "pill-shaped structure" serves as a pressure chamber to accommodate the propellant. This pill shaped pressure chamber is securely pressed or jammed in its edge area between the edge along its circumference—as previously described for the partition—between the edge areas of the upper part of the chamber and the lower part of the chamber.

The sealing of the pressure chamber may take place in a suitable manner, such as by means of sealing rings made of a suitable material, such as elastomers, e.g. silicon-O-rings, or metals or by glueing with a suitable adhesive, e.g. with 2-component resins.

The filling of the pressure chamber with the propellant can take place after removal of the existing air from the pressure chamber (e.g., by aspiration) in any suitable manner. It is possible, for example, to introduce a microcapillary through the sealing surface through which the propellant may be filled into the pressure chamber. After the filling with the propellant the capillary can be plugged or withdrawn.

All propellants that are usually used in implantable infusion pumps may serve as a propellant. Preferably, the propellant hexafluorobutane is used as a propellant according to the invention, whereby 1,1,1,4,4,4-hexafluorobutane is preferred in particular. Implantable infusion pumps containing these propellants are described in the application simultaneously submitted with this application under file no. P 195 09 632.0-35 with the title "Implantable Infusion Pump" (Our reference FR2664)

The implantable infusion pumps having the previously described flexible gas impermeable partition, or the "pill shaped" pressure chamber may be designed in any suitable manner and made of any suitable biocompatible material, such as, metal or plastic. Preferably, they are made of plastic, whereby hard plastics such as polysulphones (including polyethersulphones), polyamides and polycarbonates, in particular poly sulphones are preferred. The use of infusion pumps made of plastic provides substantial advantages. In addition to lower weight in comparison to infusion pumps made of metal, infusion pumps made of plastics provide the prerequisites for the simultaneous application of certain diagnostic procedures such as thermography and MRI.

In particular the infusion pumps are designed as described in DE 44 32 991 A1.

In the implantable infusion pump no or essentially no gas diffusion through the flexible partition occurs. The implantable infusion pump according to the invention guarantees a constant pumping rate for the entire operational time. It has a low weight, is easy to, simple and safe to handle, and simple and cost effective to produce.

The infusion pump allows up to a maximum of 120 fillings with medicinal solutions whereby the pumping rates per day are, for example, 0.7, 1.0, 1.4, or 2.0 ml and the medication reservoir can accommodate approx. 30 ml of the medicinal solution. The amount of the propellant added is small and may, for example, be 2 ml. The inner volume of the pressure chamber may be 40 ml, for example.

The infusion pump is suitable for the administration of a continuously dosed administration of medication such as e.g. heparin, artificial pancreatic insulin, chemotherapeutic agents, pain relievers, such as morphine, muscle relaxants, such as baclofen, and the like.

The following examples serve to further explain the present invention.

EXAMPLE 1

FIG. 1 represents a vertical section through a schematically depicted implantable infusion pump according to the invention.

The infusion pump 1 is a disk shaped rotationally symmetric body made of hard plastic with a pump chamber which is formed by a lower part of the chamber 2 and the upper part of the chamber 3 and divided by a flexible gas impermeable partition 6 into two subchambers 7 and 8. The first subchamber 7 serves as a medication reservoir and the second subchamber 8 serves as pressure chamber to accommodate the propellant.

The refilling opening 12 is sealingly covered by a pierceable central septum 13 and is provided beneath the central septum 13 with a refilling space with a fixed plate serving as a needle stop and a passage openings to the medication reservoir 7.

The flexible gas impermeable partition 6 is convex following the contour of the upper part of the chamber 3 (and accordingly the lower part of the chamber 2) which was achieved by deep drawing. This partition is stress free. It consists of a film system which, seen from the medication reservoir 7, is composed as follows:

a) film made of polyethyleneterphthalate, thickness 100 $\mu$m
b) film made of polychlorotrifluoroethylene, thickness 127 $\mu$m
c) composite aluminum film made of
  i) polyethyleneterphthalate film, thickness 12 $\mu$m
  ii) aluminum foil, thickness 12 $\mu$m
  iii) polyethylene film, thickness 70 $\mu$m The films of the aluminum composite film are joined together by means of a polyurethane adhesive. The films a) and b) are joined together with the aluminum foil in the edge area along the entire circumference only. The partition 6 is jammed or pressed between the edge areas of the upper chamber part 3 and the lower chamber part 2 with its outer edge area along its entire circumference.

EXAMPLE 2

Figure 2:
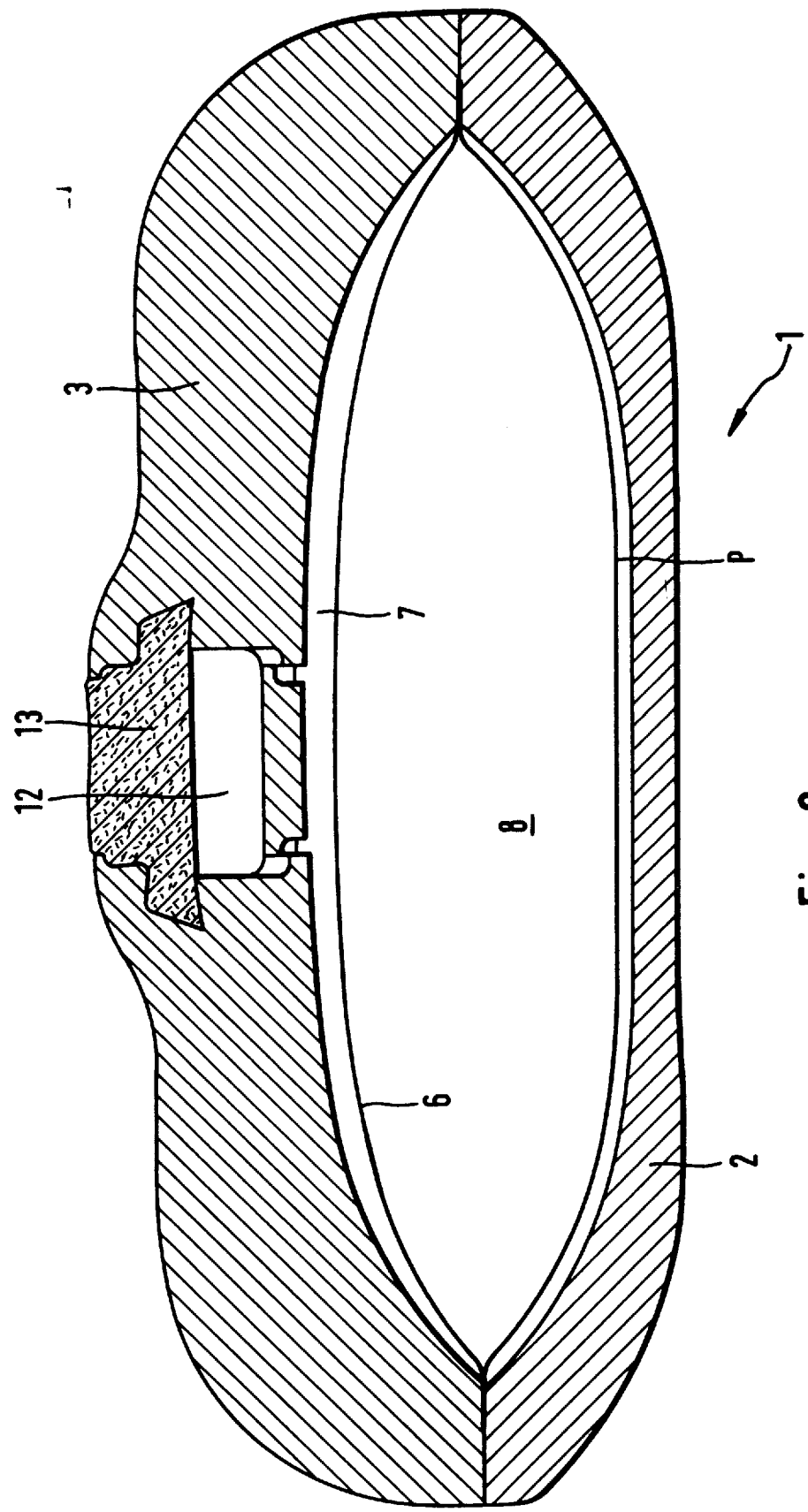
FIG. 2 also depicts a vertical section of an additional schematically depicted implantable infusion pump.

FIG. 2 also depicts a vertical section of an additional schematically depicted implantable infusion pump.

This infusion pump corresponds to the infusion pump depicted in FIG. 1 according to example 1 with the exception that in addition to partition 6 a convex composite metal film P is also disposed. This composite metal film P is made convex by deep drawing following the contour of the inner wall of the lower part of the chamber 2 and joined along the edges of the entire circumference of the partition 6 which has the same composition as the partition described according to example 1. The composite metal film P—seen from the pressure chamber 8—is composed as follows:

i) polyethylene film, thickness 70 $\mu$m
ii) aluminum foil, thickness 12 $\mu$m
iii) polyethyleneterphthalate film, thickness 12 $\mu$m According to this example a pill-shaped pressure chamber 8 is formed by the partition 6 and the metal composite film P This pressure chamber is, as described in example 1, jammed or pressed between the edge areas of the upper chamber part 3 and the lower chamber part 2 with its edge area along its entire circumference.

As a propellant 1,1,1,4,4,4-hexafluorobutane is used and is brought into the pressure chamber in that a microcapillary is introduced through the sealing surface in the edge area, the air removed from the pressure chamber and the pressure chamber filled with the propellant through the microcapillary. The amount introduced was approx. 2 ml.

The inner volume of the pressure chamber 8 is approx. 40 ml and the medication reservoir can accommodate approx. 30 ml of the medicinal solution.

EXAMPLE 3

Figure 3:
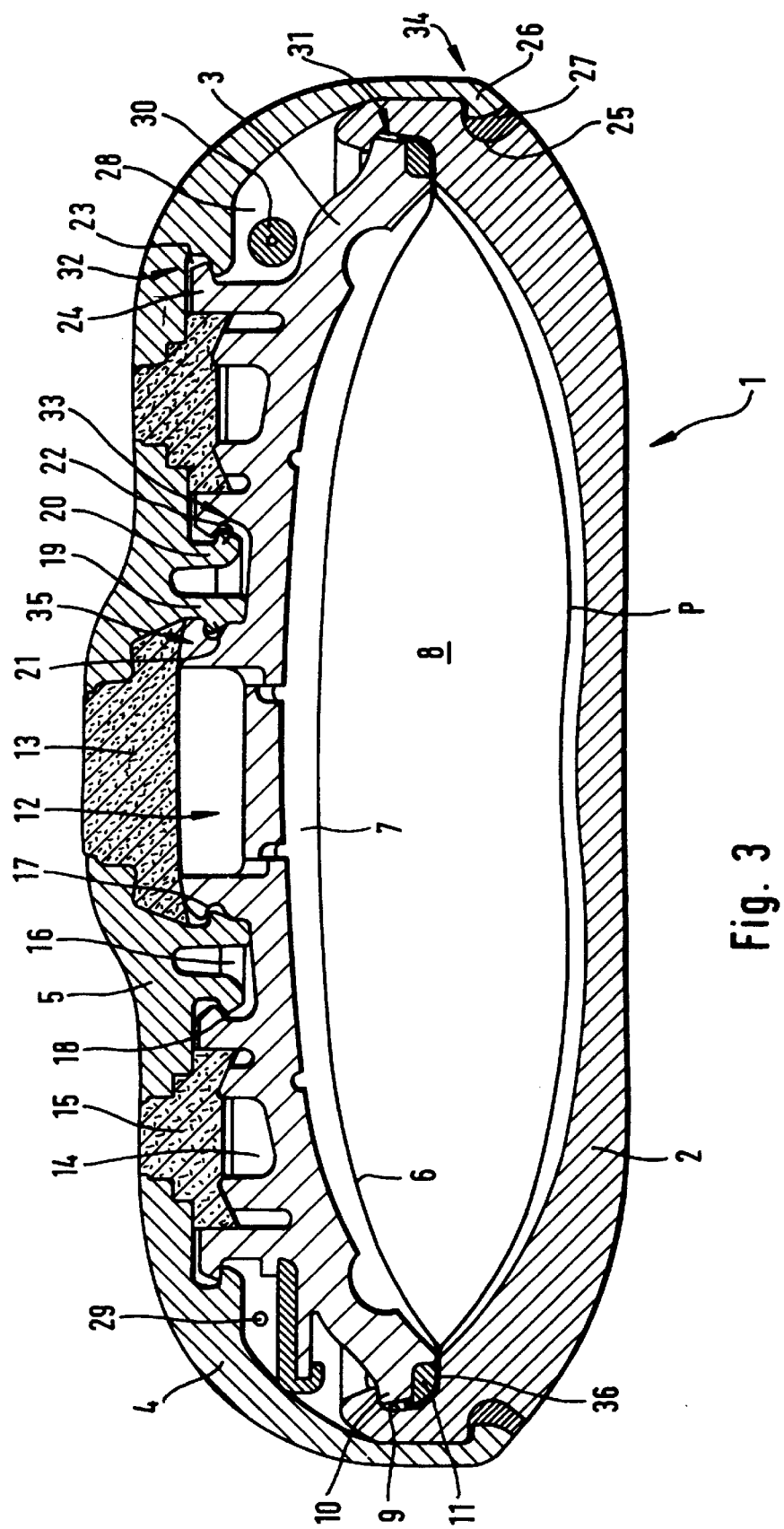
FIG. 3 depicts a vertical section through a specially designed infusion pump for the dosed administration of medication into the human body.

FIG. 3 depicts a vertical section through a specially designed infusion pump for the dosed administration of medication into the human body.

The infusion pump 1 is a disk shaped rotationally symmetric body made of polysulphone, with a housing that consists of a shell-shaped lower chamber part 2, an upper chamber part 3 executed in an opposing convex shape, a clasp 4 and a septum holder. The inner space is divided by a convex partition 6 and a likewise convex aluminum composite film P into a first subchamber serving as a medication reservoir 7 and a second subchamber serving as a pressure chamber 8 for the acceptance of the propellant. The pressure chamber 8 is formed by welding or glueing of the edge of the partition 6 and the aluminum composite film and is shaped in the form of a pill. An annular groove is molded at the upper inner edge area of the lower part of the chamber 2 into which [groove], as a snap-in joint, a circumferent corresponding edge 10 of the upper part of the chamber 3 together with an O-ring 11 and one edge 36 formed by the partition 6 and the aluminum composite film P is snapped and sealed.

A refilling opening 12 is sealingly covered by a pierceable central septum 13 and has, beneath the central septum 13, a refilling space with a fixed plate serving as a needle stop and passage openings to the medication reservoir 7.

Furthermore, on the upper side of the upper chamber part 3, a concentric annular chamber 14, which is sealingly covered by a ring septum 15, is molded.

Between the annular chamber 14 and the refill opening 12, a concentric annular groove 16 is molded on each of whose internal and external side walls a circumferent snap-in groove 17, 18 is provided. The annular septum holder 5 overlaps with its internal edge the edge of the disk shaped central septum 13 and with its external edge the inner edge of the ring of ring septum 15. Furthermore, septum holder 5 engages the annular groove 16 with the adjacent ring webs 19, 20, whereby the latches 21, 22 engage the snap-in grooves 17, 18 at the ring webs 19, 20.

The annular outer edge of the ring septum 15 is covered in a stepped arrangement by an appropriately shaped edge area of the clasp 4 and sealingly jammed against the upper chamber part 3. Furthermore, in this edge area of the clasp 4 a snap-in joint is provided between the clasp 4 and the upper chamber part 3 which [joint] consists of a circumferent snapping groove 23 on the clasp 4 and a circumferent latch 24 on the upper chamber part 3.

On the external lateral edge area of the lower chamber part 2, an additional annular groove 25, which engages a circumferent latch 26 together with an inserted O-ring 27, is molded. The latch 26 represents the lower edge of the clasp 4, whereby said clasp overlaps the side area of the upper chamber part 3 and the external edge area on the side of the lower chamber part 2 in a bell shape. The clasp 4 is supported (when stressed by high pressure) on the upper chamber part 3 by means of the latch arrangement 24 and by means of the annular septum 25 towards the lower chamber part 2.

Between the external wall area of the upper chamber part 3 and an inner wall area of clasp 4 an annular space 28 is formed to accommodate an outlet reduction arrangement 29 (here schematically depicted as a section through a capillary) and an outlet catheter 30.

The connection 31, formed by the annular groove 9, the edge 10 and the O-ring 11, the connection 32, formed by the snapping groove 23 and the latch 24 as well as connection 33 consisting of snapping groove 18 and the latches 22 are the primary joints which essentially support the internal pressure stresses occurring from loads from normal operational use.

The connection 34, consisting of annular groove 25, the latches 26 and the O-ring 27 as well as connection 35, consisting of the snapping groove 17 and the latches 21, are secondary joints which have no or at least a very slight support function under normal operational use. The secondary joints 34, 35 provide support function by increased pressure above normal operational pressure only, in particular in the case of failure of the primary joints 31, 32, 33.

The primary joints 31, 32, 33 are hereby in constant engagement and ensure the integrity of the implanted infusion pump under normal operational conditions. With an increase of the internal pressure either in the annular space 28 or in the medication reservoir 7, the secondary joints 34, 35 increasingly engage. Hereby the stresses are transferred from the primary joints 31, 32, 33 and are distributed to primary and secondary joints.

If, for example, the primary joint 31 should fail, the connecting task is taken over by the secondary joint 34. Since a gap simultaneously occurs between the upper chamber part 3 and the lower chamber part 2, medication escapes into the annular space 28 between the clasp 4 and the upper chamber part 3 thus causing the total pressure and thus the stress of the joint to decrease. This enables the secondary joint 34 to guarantee the integrity of the infusion pump to the outside. It is essential here that the lower part fail in the upper area of the latches but not in the lower part which can be secured by design.

In the event of a failure of the primary joint 32 between the upper part of the chamber 3 and the clasp 4, the connection is likewise taken over by the secondary joint 34.

Correspondingly, in case of a failure or an overload of primary joint 33, a takeover or a distribution is transferred to the secondary joint 35.

In any case it is advantageous that secondary joints 34, 35 are available in case of an overload or a failure of the primary joints 31, 32, 33, thus guaranteeing a safe continued operation of the infusion pump 1 thus substantially improving patient safety.

The partition 6 used in this example correspond to the partition 6 and the aluminum composite film used in example 2 with regard to its composition as well as its shape. The pill shaped pressure chamber 8 has an inner volume of 40 ml and contains approx. 2 ml of 1,1,1,4,4,4-hexafluorobutane as a propellant. The medication reservoir can accommodate up to 30 ml of medicinal solution. This infusion pump allows up to a maximum of 120 fillings with the medicinal solution and daily pumping rates of 0.7, 1.0, 1.4 or 2.0 ml of medicinal solution.

What is claimed is:

1. An implantable infusion pump for the dosed administration of medications into the human body, comprising:
   a pumping chamber, which is formed by a lower chamber part; and an upper chamber part connected thereto, wherein a) the pumping chamber is divided by a gas impermeable flexible divider into two subchambers;

b) the first subchamber is delimited by the upper chamber part and the flexible partition and is designed as a reservoir for medicinal solutions, the upper part of the chamber has a refill opening which is sealed by at least one pierceable septum, and the reservoir for medicinal solutions is connected to an outlet catheter via an outlet opening, and c) the second subchamber is delimited by the lower chamber part and the flexible partition and is designed as a pressure chamber to accommodate a propellant, wherein the gas impermeable flexible divider is a convex metal foil following the contour of the inner form of the upper part of the chamber and is covered with a first polymer film on the side facing the medicinal solution.

2. The infusion pump according to claim 1, wherein on the side of the metal foil facing the medicinal solution, a third polymer film with good blocking characteristics against water vapor is disposed.

3. The infusion pump according to claim 2, wherein the third polymer film is a polychlorotrifluoroethylene film.

4. The infusion pump according to claim 1, wherein a fourth polymer film with medication compatibility and blocking characteristics against water vapor, oxygen and $CO_2$ coming in contact with the medicinal solution, is disposed.

5. The infusion pump according to claim 4, wherein the fourth polymer film is a polyethyleneterephthalate film.

6. The infusion pump according to claim 1, wherein a second metal foil or a metal composite film is additionally disposed between the propellant and the inner wall of the lower part of the chamber which film is connected to the partition in the edge area along the entire circumference.

7. The infusion pump according to claim 6, wherein the second metal foil is made of platinum.

8. The infusion pump according to claim 6, wherein the second metal foil is made of aluminum.

9. The infusion pump according to claim 6, wherein the second metal foil is made of gold.

10. The infusion pump according to claim 6, wherein the second metal foil is made of silver.

11. The infusion pump according to claim 6, wherein the second metal foil is made of titanium.

12. The infusion pump according to claim 1, wherein the first polymer film of the metal foil facing the medicinal solution is a film made of polyamide.

13. The infusion pump according to claim 1, wherein the first polymer film of the metal foil facing the medicinal solution is a film made of polyethyleneterephthalate.

14. An implantable infusion pump for the dosed administration of medications into the human body, comprising:

a pump chamber, which is formed by a lower chamber part; and an upper chamber part connected thereto, wherein a) the pumping chamber is divided by a gas impermeable flexible divider into two subchambers, b) the first subchamber is delimited by the upper chamber part and the flexible partition and is designed as a reservoir for medicinal solutions, the upper part of the chamber has a refill opening which is sealed by at least one pierceable septum, and the reservoir for medicinal solutions is connected to an outlet catheter via an outlet opening, and c) the second subchamber is delimited by the lower chamber part and the flexible partition and is designed as a pressure chamber to accommodate a propellant, wherein the gas impermeable flexible divider is a convex metal foil following the contour of the inner form of the upper part of the chamber and is covered with a first polymer film on the side facing the medicinal solution and a second polymer film on the side facing the propellant.

15. The infusion pump according to claim 14, wherein the second polymer film is a polyolefin film.

16. The infusion pump according to claim 15, wherein the polyolefin film is a polyethylene film.

* * * * *